United States Patent [19]
Hohn

[11] Patent Number: 4,768,165
[45] Date of Patent: Aug. 30, 1988

[54] COMPUTER INTERFACE UNIT FOR AN AUDIOMETER

[75] Inventor: Werner H. Hohn, Uttenreuth, Fed. Rep. of Germany

[73] Assignee: Siemens Aktiengesellschaft, Berlin and Munich, Fed. Rep. of Germany

[21] Appl. No.: 777,664

[22] Filed: Sep. 19, 1985

[30] Foreign Application Priority Data

Oct. 2, 1984 [DE] Fed. Rep. of Germany ....... 3436127

[51] Int. Cl.$^4$ .......................... H04R 29/00; G06F 3/00
[52] U.S. Cl. ..................................... 364/900; 73/585; 73/584; 381/68.2
[58] Field of Search ... 364/200 MS File, 900 MS File; 73/585, 584; 179/1; 381/68.2, 74

[56] References Cited

U.S. PATENT DOCUMENTS

| | | | |
|---|---|---|---|
| 3,808,354 | 4/1974 | Freezor et al. | 73/585 |
| 4,157,456 | 6/1979 | Voss | 179/1 N |
| 4,224,468 | 9/1980 | Calder, Jr. | 73/585 |
| 4,284,847 | 8/1981 | Besserman | 73/585 |
| 4,321,427 | 3/1982 | Singh | 73/585 |
| 4,327,252 | 4/1982 | Tomatis | 179/1 N |
| 4,356,825 | 11/1982 | Veth | 128/630 |
| 4,390,748 | 6/1983 | Zwicker | 179/1 N |
| 4,448,074 | 5/1984 | Schmidt | 73/585 |
| 4,489,610 | 12/1984 | Slavin | 73/585 |
| 4,548,082 | 10/1985 | Engebretson et al. | 73/585 |
| 4,637,402 | 1/1987 | Adelman | 128/746 |

OTHER PUBLICATIONS

Self-Test and Serviceability for Dependable Central Patient Monitoring, Hewlett-Packard Journal, Nov. 1980, pp. 19–23.

*Primary Examiner*—Gary V. Harkcom
*Assistant Examiner*—Randy W. Lacasse
*Attorney, Agent, or Firm*—Mark H. Jay

[57] ABSTRACT

An interface unit for measuring instruments, such as audiometers, which are controlled by a computer, the interface unit being as cost-efficient as possible and setting minimum requirements for the computer hardware and software. This is achieved in that the lines (17 to 19) of the interface unit that are connected to the computer contain d-c isolating couplers (17.1 to 19.1) and are respectively connected with individual decoders (13 to 15) which, in turn, are connected to memories (7 to 9). Control lines lead from these memories to the measuring modules (1 to 3) of a measuring instrument. Such a measuring instrument is usable, in particular, as an audiometer or for establishing the optimum adjustment of a hearing aid to compensate certain hearing impairments.

19 Claims, 2 Drawing Sheets

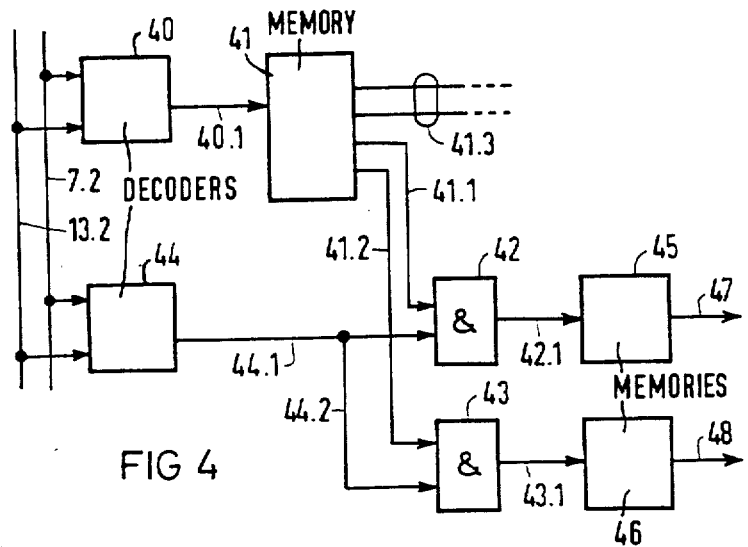
FIG 4
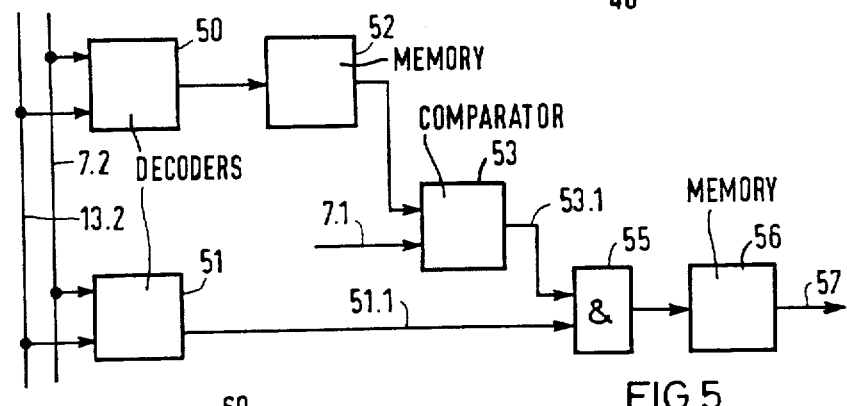
FIG 5
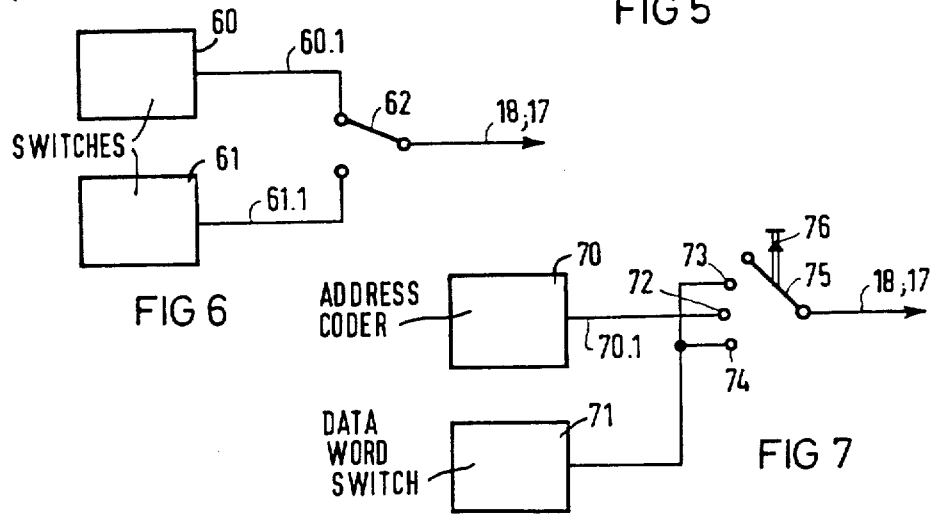
FIG 6
FIG 7

COMPUTER INTERFACE UNIT FOR AN AUDIOMETER

BACKGROUND OF THE INVENTION

The invention relates to a computer interface unit for a measuring instrument such as an audiometer. Such instruments are known for instance from the British Pat. No. 1,599,367.

If such a measuring instrument is to be automatically controlled by a computer, all control processes, as for example the selection of volume or frequency response, must be electronically remote-controllable. In addition, provision must be made that the control lines, required in large number, can be operated successively by a few computer control lines, and that the selected functions remain set until changed. As is known, tasks such as these are performed by computer interfaces.

Known interfaces, are too complicated to be usable with each measuring module of instruments that are used in practice. In addition, known interfaces require signal sequences which extremely simple computers, such as are used in audiometry or hearing aids, cannot supply without additional hardware.

To construct a low-cost instrument for manual operation which can be easily adapted for automatic control by a computer, the modules to be operated—e.g., the sound generator, the volume control, etc., of an audiometer—must be controllable by simple manual switches. Such an arrangement is advantageous also in computer-controlled measuring instruments because, in case of error, the manual override of the computer by the manual switches makes it possible to determine which errors had previously been caused by the computer alone. Conventional interfaces are not fully suitable for this task, as their operation is too complicated.

Audiometers employed in the medical sector are continually subject to increased requirements for electrical safety. However, it is often required to connect the instruments to outside computer components, e.g., to central computers of a company which meets lower safety requirements. For this reason a d-c isolation must be provided for the higher stipulated differential voltage between the computer and the components to be controlled or between the computer and the outside computer components. The first solution is more favorable because it eliminates the disturbance of the sometimes extremely weak useful signals of the audiometer by the d-c coupling with the control signals of the computer.

Inexpensive coupling elements, such as optocouplers, for differential voltages over 4 kV, result in time differences of the control signals during parallel transmission as required for rapid control processes. Here the conventional interfaces require additional expenditure for reliable operation, e.g., in the form of delay compensating circuits.

SUMMARY OF THE INVENTION

It is an object of the present invention to provide an inexpensive interface unit for connecting a controlling computer to an audiometer that has a plurality of controllable circuit modules.

It is a further object of the present invention to provide such an interface unit which places extremely modest requirements on the computer hardware and software.

It is a further object of the present invention to provide such an interface unit which permits d-c isolation between the computer and the audiometer by means of a minimum number of extremely voltage-stable coupling elements.

These objects, as well as further objects which will become apparent from the discussion that follows, are achieved, according to the present invention, by providing an interface unit having a plurality of first control lines connectable to the computer, each having a d-c isolating coupler therein; a plurality of decoders, connected to these first lines; a plurality of memories, each connected to one of the decoders; and a plurality of second control lines connecting the memories with the audiometer modules.

The invention makes it possible to implement the following features:

1. Individual modules of the measuring device are combinable at will and their control is extremely interference-proof.

2. The control process does not disturb the signals for the hearing test, whose voltage may be in the $\mu V$ range.

3. The modules can signal their presence to the computer, on demand, by reply signals, and can convey measurement results, independently of the control lines for program branching.

4. The interface unit is to be constructed so that the modules can be operated also without the interface via several switches, or with the interface but manually without the computer.

5. To suppress switching interference such as noises, the hardware automatically generates a blanking signal.

An interface unit according to the invention achieves these objects (1) if at least two signal lines are used for the actuation of the audiometer (preferably eight lines are used for signalling the audiometer from the computer, and preferably one signal line is used for the reply to the computer for the audiometer), (2) if the address words of the individual modules and the data words are transmitted alternately one after the other, and (3) if each data word following an address word is stored, after a preselectable waiting time without a clock signal transmitted by the computer, in a data memory assigned to this address. Due to the fact that the actuating signals and the reply signals are conducted over separate lines, relatively expensive switching components in every module are eliminated. The interleaving of address words and data words reduces the costs for the d-c isolation and for the connection of each module with the computer by manual wiring or by means of a mother board.

In order to eliminate the effects of interference pulses on the data bus (which interference pulses might result in a wrong address) the invention provides that the waiting time between the disconnection of the address word and the acceptance of the following data word is brought about by integration of the output signal of the respective address decoder.

To fulfill the above-mentioned requirements, furthermore, a part of the data words—the maximum permitted by the number of control lines—is reserved for addresses, and the address decoder is constructed so that it automatically generates a control signal of selectable duration which, during the execution of commands, can blank out interference voltages caused by the switching of the desired signal paths. As an example, the earphone output can be briefly turned off with a "soft"-switching optocoupler.

In addition, a reply signal is also generated, which for example can turn on a luminous display to indicate that the command memory belonging to an address has been readied for the acceptance of new data, or which informs the computer whether a program transfer, that would require the function just then addressed, is possible.

To minimize the number of lines, the signal flow of a selectable portion of the control lines can be reversed. The reversal can be brought about by a computer command or automatically after the time out of a delay element started by the respective address decoder, for a selectable period. This permits a rapid parallel transmission of test data, for example of the reaction or response time to a stimulus of a test subject, from the audiometer to the computer for evaluation.

Microcomputers efficient enough for an audiometer generally have a data output with eight lines, which can also be switched over and used as an input, and often they have an additional data input with at least one line. In order that the audiometer can be controlled by different computers, preferably eight control lines are provided, and the reply signals of all address decoders are transmitted via a single reply line by means of OR circuits.

The reply signals for the identification of modules having the same address, as for example a tone generator and a locked-in filter, can be transmitted with different delays, after their address has been turned off, so that also in this case the presence of all modules required for a program branch can be tested by counting the replies.

For polling test data present in the audiometer in the form of a bit pattern, a separate address decoder is provided, for each bit, whose reply signal is influenced by the state of the associated bit. This means for example that a reply signal is given only when the associated bit is set. By serial selection of these address decoders the computer can poll the bit pattern.

If one module requires more than two address decoders, it has been found desirable if a first address word and a first data word define a sub-address under which, with the aid of a second address, a second data word is stored. In this case, the total number of components for command storage is smaller than for one address decoder per command memory. It is, of course, possible to combine several modules in this manner.

To achieve high immunity to interference, all control and reply lines can be d-c isolated from the computer for instance by means of optocouplers for differential voltages higher than 4 kV. The measuring instrument modules can then be operated with freely selectable control voltages, which may differ considerably from those of the computer. They can be operated for example with voltages between $U_{low} = -7.5$ V and $U_{high} = +7.5$ V, in order to switch a-c voltages without bias and without level shifting using standard CMOS components.

For high immunity to interference, all commands may first be stored temporarily and then stored permanently only in case of coincidence when the address and data word are repeated. As a result of this, an interference pulse which simulates a wrong address will not lead to an adjustment of the audiometer that might harm the test subject, e.g., an adjustment establishing an excessive volume.

For the construction of a simple, manually-operated audiometer, an address and a data word can each be selected with a separate multi-pole switch. With a multi-pole reversing switch it is then possible first to switch to the bus the first address, then the respective data word; thereafter, after changing the address switch, the second address, and after changing the data word switch, the second data word. The particular state of the command memory can be indicated for control, e.g., by light-emitting diodes or liquid crystal displays.

If a separate command selector switch for each address is provided, the particular address can be hardwired, switching with a multi-pole step switch or key with at least three positions from the off state via the address to the respective command. Provision must be made that, before the off state is reached again, the address is not repeated without a command. This results in the advantage that the user can operate such an audiometer in same manner as he is accustomed to from the earlier manually-operated instruments.

By applying the present invention, it would be possible, for example, to improve the computer-controlled audiometer according to the U.S. Pat. No. 3,808,354, the audiometric computer according to the U.S. Pat. No. 3,970,785, and the audiometer according to the Canadian Pat. No. 950,106 by equipping all modules, as e.g. oscillator or noise generator, with address decoders and command memories for e.g. nine signal lines. In this way even the simplest personal computers can be utilized without alteration. Signals for interference voltage blanking are available in the interface without additional equipment for circulating.

It is true of all computer-controlled audiometers that, through the use of isolating elements, such as optocouplers, in the above-described manner between the computer and the instrument the stricter safety rules can be fulfilled at lower cost than by shielding and insulating the various parts. In particular, it is not necessary to insulate the parts used by the test subject, as e.g., the headsets, or to provide special power isolating transformers for the computer and its periphery and an additional protective disconnect point in the connection to external data processing systems.

Further it is possible in a simple manner to connect a manual control console instead of a computer, in case the user wishes to save the expense of a computer, and to carry out hearing tests in the familiar manner used with mechanically operated audiometers.

Audiometers with many earphones for the simultaneous testing of several persons, for example according to the U.S. Pat. No. 3,808,354 or the British Pat. No. 1,599,367, could be improved by the invention since the computer may automatically recognize the number of connected modules associated with a test subject, or the presence of modules for special tests, and carry out the respective program branches.

In many audiometers, and in particular in fully automated ones, as disclosed, for example in the Canadian Pat. No. 950,106, the control of the output signals according to the invention and the reporting of errors/faults to the computer achieve the advantage that the test subject is asked automatically to use a different headset.

For a full understanding of the present invention, reference should now be made to the following detailed description of the preferred embodiments of the invention and to the accompanying drawings.

BRIEF DESCRIPTION OF THE DRAWINGS

FIG. 4 is a block diagram of a simplified construction of the decoder-memory combination.

FIG. 5 is a block diagram of a safety device which can be employed in the transmission of data for the control of the modules against faulty control.

FIG. 6 is a block diagram of a circuit including a multi-pole switch for manual operation of the measuring instruments without a computer.

FIG. 7 is a block diagram of a particular design of the multi-pole switch according to FIG. 6.

DESCRIPTION OF THE PREFERRED EMBODIMENTS

Figure 1:
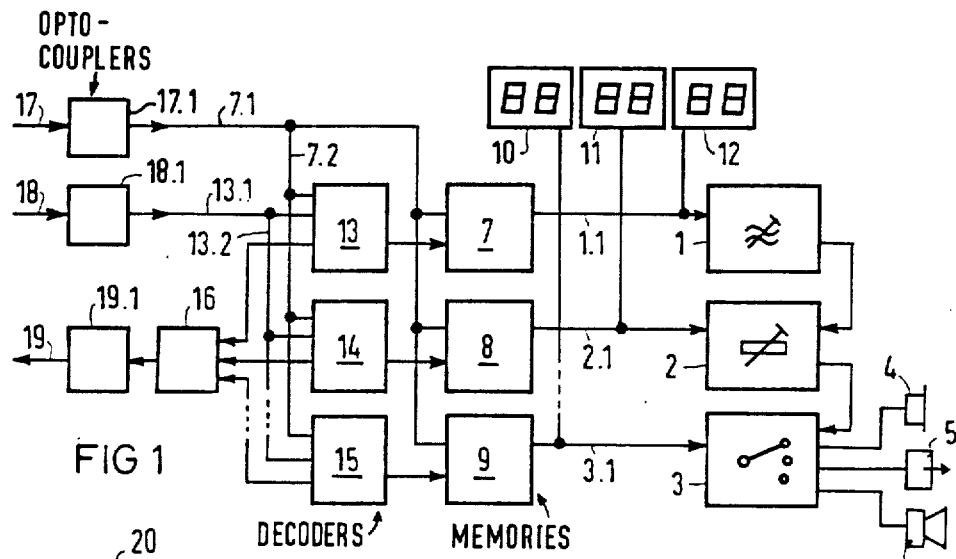
FIG. 1 is a block diagram of an interface, according to the invention, which connects a computer to an electronically controllable audiometer.

In FIG. 1, the reference numeral 1 denotes a tone generator which is connected via a level selector 2 and a selector switch 3 for the actuation of one of the several acoustic transducers 4 to 6. To transmit the test sound to a person to be tested there are available an earphone 4 to be applied to the ear, a vibrator 5 which transmits acoustic vibrations to the skin, and a loudspeaker 6. The particular function of the modules 1 to 3 of the audiometer is determined by means of the data memories 7 to 9. The current value of adjustment is then visible on the alphanumeric display panels 10 to 12.

To set the audiometer, signals are transmitted by a computer (not shown) via lines 17 and 18, the signals passing from address decoders 13 to 15 into the memories 7 to 9, respectively. To avoid interference it is assumed that the associated address is disconnected after a minimum hold time, which is longer than the expected duration of the interference.

During the time that an address associated with the respective decoder 13 to 15 to be addressed is present, a reply signal coming from one of these decoders 13 to 15 is transmitted to the computer via an OR gate 16 and an optocoupler 19.1.

Optocouplers 17.1 and 18.1 are provided in the control lines 17 and 18, respectively, in order to obtain a d-c isolation of the computer from the audiometer. Here line 17 as well as the continuation line 7.1 for data transmission may be laid out sevenfold. Also the line 1.1 between the memory 7 and the tone generator 1, the line 2.1 between the memory 8 and the level selector 2, as well as the line 3.1 between the memory 9 and the selector switch 3 may, in adaptation to the requirements of the control modules 1 to 3, be laid out sevenfold. With the sevenfold layout corresponding to line 17, the number of decoders 13 to 15 and of data memories 7 to 9 can be increased to 128.

Figure 2:
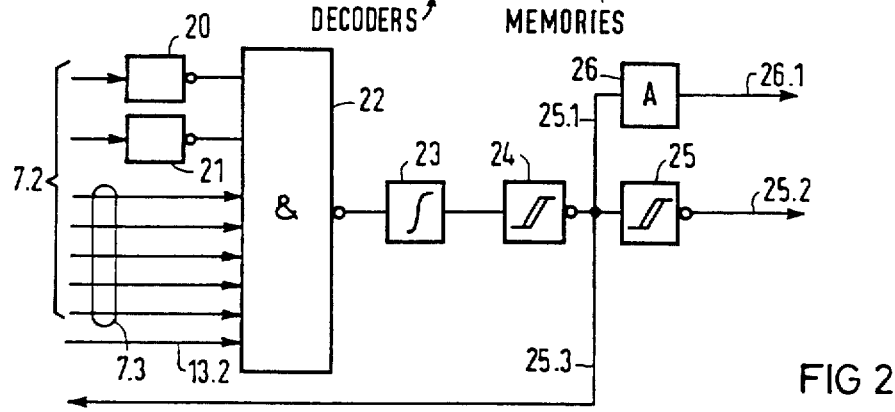
FIG. 2 is a basic block diagram of the decoders connected at the input of the interface according to FIG. 1.

In FIG. 2, the reference numerals 20 and 21 denote blocks which invert the signals coming from the computer. These signals, as well as those of lines 7.3, then go to a NAND gate 22, where they are evaluated. To eliminate the effect of interference pulses, the output signal of this gate then goes to an integrator 23 and via Schmitt trigger inverters 24 and 25 to an output line 25.2. A line 25.1 branches off from the output of inverter 24 and leads to a monostable multi-vibrator 26 which, for a certain period in the order of 20 msec to 0.2 sec, furnishes a control signal on line 26.1 for interference blanking. This signal on line 26.1 controls a switch which disconnects the output signal of the level selector 2. Line 25.2 is connected to the respective memory 7 to 9. Line 25.3, branching off between the inverters 24 and 25, carries the reply signal to the OR gate 16.

Figure 3:
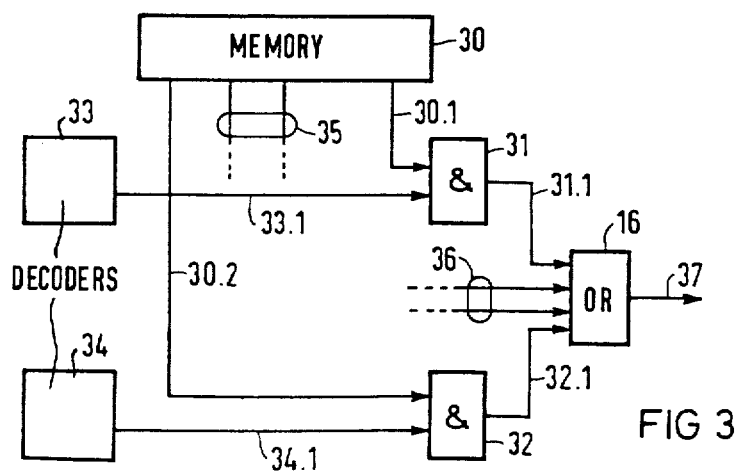
FIG. 3 is a block diagram of an arrangement for the transmission of test results from the audiometer to the computer.

FIG. 3 shows a bit pattern memory 30 for test values which are determined by the audiometer itself. Such a signal pickup may represent, e.g., the time period between the beginning of a stimulus and the associated depression of a response key by the test subject. An AND gate 31 is connected to the memory 30 via a line 30.1. A second input of this AND gate is supplied the reply signal of decoder 33 via line 33.1. Thus a reply signal is supplied to the OR gate 16 via line 31.1 only when a) the address associated with decoder 33 is present and b) the memory output line 30.1 carries a "1" bit of the bit pattern memory 30. If this is not the case, the computer receives no reply signal when it transmits the address of decoder 33.

Similarly, the reply signal of decoder 34 is forwarded to the OR gate 16 only when another output line 30.2 of the memory 30 is high.

As indicated by dashed lines 35 in FIG. 3, additional memory locations of the memory 30, receiving the bit pattern to be transmitted to the computer, can influence the forwarding of the reply signals from additional decoders (omitted in the drawing), with the aid of additional AND gates (not shown), to the OR gate 16 via one of the lines 36. By serial selection of all address decoders which are associated with the memory 30, the computer can poll the bit pattern. Line 37 leads to the computer via the optocoupler 19.1.

FIG. 4 illustrates an arrangement where a first address and a first data word define a sub-address, where a second data word is stored by means of a second address. This takes place when a store command is transmitted by signals from the computer, via the lines 7.2 and 13.2, a decoder 40 and a line 40.1, to a memory 41. This memory 41 controls the transmission of store commands of a decoder 44 which are passed to command memories 45 and 46 via lines 41.1 and 41.2 as well as by AND gates 42 and 43. The dashed lines 41.3 indicate the possible expansion by additional further AND gates and memories. The forwarding of the stored control signals to modules such as the tone generator 1 or level selector 2, etc., occurs via lines 47 and 48.

The arrangement according to FIG. 5, achieves a high immunity to interference in that all commands intended for the memory 56 are first temporarily stored in the memory 52 and then stored permanently only after coincidence with a repeat of the address and data word. To this end, decoders 50 and 51 are connected with and receive signals from the computer via lines 7.2 and 13.2. From decoder 50 a store command passes to a memory 52 and from there to a comparator 53. The respective valid data word transmitted on the seven lines 7.1 is also supplied to the comparator 53.

The comparator 53 and the decoder 51 are connected to an AND gate 55 via lines 53.1 and 51.1, respectively. Thus the memory 56 receives a store command only when (a) the comparator 53 signals coincidence of the stored data word with the one just then present on the bus and (b) decoder 51 generates a store command. Control signals can be sent to the modules via a line 57.

FIG. 6 shows a multi-pole reversing switch 62 which can switch bit patterns onto the lines 17 to 18 of FIG. 1 in place of a computer. Either an address word or a data word can be selected by the eight-pole switch 60 (two hexadecimal switches) or the seven-pole switch 61, respectively. These words can be sent alternately through the switch 62 to the data and address bus consisting of the lines 17 and 18. A given command is terminated always by a data word and not by an address word. The line 18 is supplied only by the address selector 60.

In FIG. 7 are illustrated a permanently wired address coder 70, a data word switch 71, and a multi-pole reversing switch 75. A separate one of each of these devices is provided for each audiometer module to be controlled, so as to be able to operate with manual control instead of computer control. The switch arm 75, which, as indicated by an arrow 76, is biased into the off position by a spring, operates in such a way that it is possible to switch from the off state via the command present at the switching points 73 and via the address present at the switching points 72 again to the command also present at the switching points 74 and back to the off state, a command operation being terminated always with a command and not with an address. A mechanical, electrical or electronic interlock prevents errors from being caused by simultaneous operation of several such switches. The switching arm 75 is connected with lines 17, 18 of FIG. 1, line 18 being connected only to the address coder 70.

There has thus been shown and described a novel computer interface for an audiometer which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention which is limited only the claims which follow:

What is claimed is:

1. A computer interface unit for an audiometer having a plurality of controllable audiometer modules, said interface unit permitting control of said audiometer modules by means of a computer and comprising:
   (a) a plurality of first control lines, including both input and output lines, there being a plurality of input lines and at least one output line, the first lines being connectable to a computer and each first line having a d-c isolating coupler therein;
   (b) a plurality of decoders connected to said first lines;
   (c) a plurality of memories, each connected to one of said decoders;
   (d) a plurality of second control lines connecting said memories with said audiometer modules, whereby said audiometer modules may be controlled by said computer;
   (e) a NAND gate connected through inverters to individual ones of said input lines and without inverters to other individual ones of said input lines, said NAND gate having an output line connected via an integrator and at least one Schmitt trigger circuit to an associated one of said memories; and
   (f) an OR gate having an input connected to the line between said Schmitt triggers and an output connected to said one output line for providing a reply signal to said computer.

2. The interface unit defined in claim 1, further comprising a mono-stable multi-vibrator having an input connected to said line between said Schmitt triggers for producing an output control signal for interference blanking during a prescribed period.

3. The interface unit defined in claim 2, wherein said prescribed period is in the range of 20 MS to 0.2 seconds.

4. A computer interface unit for an audiometer having a plurality of controllable audiometer modules, said interface unit permitting control of said audiometer modules by means of a computer and comprising:
   (a) a plurality of first control lines including both input and output lines, connectable to a computer, each first line having a d-c isolating coupler therein;
   (b) a plurality of decoders connected to said first lines;
   (c) a plurality of memories, each connected to one of said decoders;
   (d) a plurality of second control lines connecting said memories with said audiometer modules, whereby said audiometer modules may be controlled by said computer;
   (e) an OR gate, having plural inputs and a single output;
   (f) a plurality of reply lines interconnecting said decoders with the respective inputs of said OR gate, the output of said OR gate being connected to said output line which has a d-c isolating coupler therein;
   (g) a second memory for storing a bit pattern, said memory having a plurality of outputs for presenting signals representing said bit pattern; and
   (h) a plurality of AND gates, each having inputs connected to one of said memory outputs and to one of said reply lines connected to a decoder, said AND gates each having an output connected to said OR gate.

5. A computer interface unit for an audiometer having a plurality of controllable audiometer modules, said interface unit permitting control of said audiometer modules by means of a computer and comprising:
   (a) a plurality of first control lines, connectable to a computer, each first line having a d-c isolating coupler therein;
   (b) a plurality of decoders connected to said first lines;
   (c) a plurality of memories, each connected to one of said decoders; and
   (d) a plurality of second control lines connecting said memories with said audiometer modules, whereby said audiometer modules may be controlled by said computer, wherein each data word is stored, following an address word and after a preselectable waiting time without a clock signal transmitted from said computer, in a data memory assigned to the respective address of such address word, the waiting time being provided by an integrator connected to receive the output signal of the address decoder, a part of the data words maximally possible through the number of control lines being reserved for addresses; wherein the address decoder is constructed so that it automatically generates a control signal for interference voltage blanking during the command execution, the duration of which is selectable, as well as a reply signal which can switch on a display; and wherein the command memory belonging to an address is prepared for the acceptance of new data and can cause a program branch in said computer.

6. The interface unit defined in claim 5, wherein the direction of signal transmission in a selectable portion of the control lines is reversable either by a computer command or, automatically, after time-out of a time delay element initiated by the respective address decoder, for a selectable period of time.

7. The interface unit defined in claim 6, wherein said computer controls said audiometer via eight signal lines.

8. The interface unit defined in claim 5, wherein the reply signals of several address decoders are supplied to said computer via at least one additional reply line by means of an OR circuit.

9. The interface unit defined in claim 10, wherein only one reply line is used.

10. The interface unit defined in claim 8, further comprising an address decoder for polling of bit patterns, there being one address decoder for each bit, the reply signal of which is influenced by the state of the associated bit.

11. The interface unit defined in claim 10, wherein only those bits of the bit pattern which are set bring about a reply signal of the associated address decoders.

12. The interface unit defined in claim 5, wherein after the disconnection of their address the reply signals for the identification of modules with the same address are transmitted with different delays.

13. The interface unit defined in claim 5, wherein a reply signal is transmitted only after it has been determined additionally by automatic measuring of the output signals of the modules that the entire audiometer operates satisfactorily, so that in case of error the computer can automatically switch to spare modules.

14. The interface unit defined in claim 5, wherein a first address and a first data word define a sub-address under which a second data word is stored at a second address.

15. The interface unit defined in claim 5, wherein to achieve high immunity to interference all control and reply lines are d-c isolated from said computer so that said audiometer modules may be operated with control voltages which differ considerably from those of said computer.

16. The interface unit defined in claim 15, wherein said d-c isolating couplers are optocouplers which permit differential voltages higher than 4 kV.

17. The interface unit defined in claim 5, wherein to achieve high immunity to interference all commands are first stored temporarily and then stored permanently only after coincidence, when the address and the data word are repeated.

18. The interface unit defined in claim 5, wherein an address and a data word are each selected with a separate multi-pole switch and are switched alternately to the bus with a multi-pole reversing switch, and wherein the particular state of the command memory is displayed to the user.

19. The interface unit defined in claim 5, further comprising (1) hardwired means for permanently providing each address of the address word and a multi-pole switch for selecting a data word; (2) a multi-pole electronic step switch controlled from the off state via the respective command and the address again to the respective command and back to the off state, and (3) means for preventing errors due to simultaneous actuation of several such switches.

* * * * *